United States Patent [19]

Bondesson et al.

[11] 3,953,601
[45] Apr. 27, 1976

[54] DIBENZOTHIOPHENE DERIVATIVES AS SERUM LIPID LOWERING AGENTS

[75] Inventors: Ulf Goran Bondesson, Huddinge; Salo Schmul Gronowitz, Lund; Nils Erik Stjernstrom, Sodertalje; Tage Rolf Gunnar Svensson, Lund, all of Sweden

[73] Assignee: Aktiebolaget Astra, Sodertalje, Sweden

[22] Filed: Feb. 28, 1974

[21] Appl. No.: 446,621

[30] Foreign Application Priority Data
Mar. 16, 1973 Sweden............................ 7303673

[52] U.S. Cl............................. 424/275; 260/329.3; 424/361; 424/362; 424/363; 424/365
[51] Int. Cl.²......................................... A61K 31/38
[58] Field of Search.................. 260/329.3; 424/275

[56] References Cited
UNITED STATES PATENTS

| | | | |
|---|---|---|---|
| 3,293,124 | 12/1966 | Bindler et al. | 424/275 |
| 3,655,697 | 4/1972 | Shen et al. | 424/275 X |
| 3,704,245 | 11/1972 | Umio et al. | 424/275 X |
| 3,736,334 | 5/1973 | Winter et al. | 424/275 X |
| 3,784,602 | 1/1974 | Frei et al. | 424/275 X |

*Primary Examiner*—V. D. Turner
*Assistant Examiner*—Vera C. Clarke
*Attorney, Agent, or Firm*—Brumbaugh, Graves, Donohue & Raymond

[57] ABSTRACT

A compound of the general formula

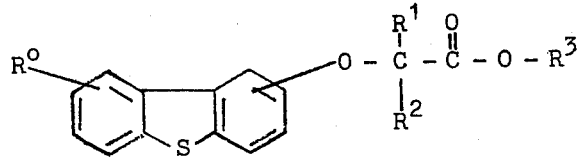

and pharmaceutically acceptable salts thereof, in which formula $R^0$ is H, F, Cl, Br or $OCH_3$; $R^1$ and $R^2$ are the same or different and selected from the group consisting of H and alkyl groups having 1–3 carbon atoms; $R^3$ is H or an alkyl group having 1–3 carbon atoms; $R^0$ and the side-chain containing the radicals $R^1$, $R^2$ and $R^3$ being placed on the same or different benzene ring. Pharmaceutical preparations containing these compounds are useful in a method for lowering the serum lipid concentration in mammals, including man. These same preparations are also useful for the combined lowering of serum cholesterol and triglyceride concentrations.

10 Claims, No Drawings

DIBENZOTHIOPHENE DERIVATIVES AS SERUM LIPID LOWERING AGENTS

The present invention relates to new compounds having valuable therapeutic properties, and therapeutically acceptable salts thereof. The invention also relates to methods for the preparation of the compounds, to pharmaceutical preparations containing them and to a method for the treatment of certain diseases by administering a therapeutically effective amount of a compound of the invention in association with a pharmaceutically acceptable carrier.

In view of accumulating evidence indicating that excessive serum lipid concentration is correlated to basic pathogenetic mechanisms and to symptoms of several diseases such as vascular diseases, diabetes mellitus, and hyperthyroidism, lowering of serum lipid concentration is important during treatment of such diseases.

A compound used for the treatment of hyperlipaemia is ethyl α-(p-chlorophenoxy) isobutyrate which compound is also named Atromidin. This compound, however, suffers from the disadvantage of giving only a minor decrease of the cholesterol concentration. Pharmaceuticals with ability to decrease cholesterol levels are known but because of the possible complications involved in simultaneous administration of two different drugs it is of great advantage to use a compound with the ability to give a combined lowering of both cholesterol and triglyceride concentration.

According to the present invention it has surprisingly been found, that compounds of the general formula $$R^O\text{-dibenzothiophene-}O-\overset{R^1}{\underset{R^2}{C}}-\overset{O}{\overset{\|}{C}}-O-R^3 \quad \text{I}$$

and pharmaceutically acceptable salts thereof, in which formula $R^o$ is selected from the group consisting of H, F, Cl, Br and $OCH_3$; $R^1$ and $R^2$ are the same or different and selected from the group consisting of H and an alkyl group with 1–3 carbon atoms; $R^3$ is selected from the group consisting of H and an alkyl group with 1–3 carbon atoms; $R^o$ and the side-chain containing the radicals $R^1$, $R^2$ and $R^3$ being placed on the same or different benzene ring; can be used for the combined lowering of both cholesterol and triglyceride concentrations.

Some of the compounds according to the invention can exist as optical isomers and the optically pure forms constitute a further aspect of the invention. In the formula I above $R^o$ is preferably H; $R^1$ and $R^2$ are preferably methyl groups and $R^3$ is preferably H or an ethyl group.

The side-chain containing the radicals $R^1$, $R^2$ and $R^3$ in the formula I above is preferably placed in position No. 4, i.e. a preferred group of compounds of the formula I can be described by the formula

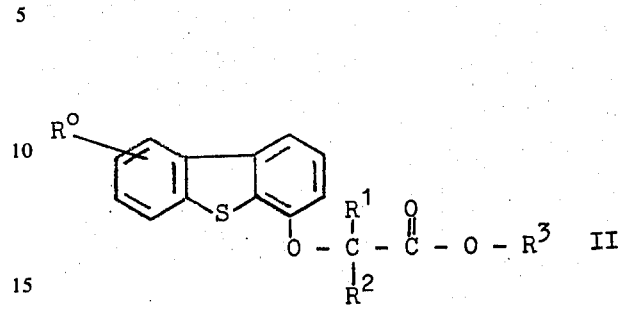

$$\text{II}$$

wherein $R^o$, $R^1$, $R^2$ and $R^3$ have the meanings given above. The preferred compound according to the invention is ethyl 2-(4-dibenzothiophenoxy)-2-methyl-propionate.

The way of indicating the position of $R^o$ and the side-chain, containing the radicals $R^1$, $R^2$ and $R^3$, in the formula I above is to designate that these two groups may be placed on the same or different benzene ring and that they can be placed at any of the eight possible positions of the two benzene rings.

The compounds according to the invention may preferably be prepared by the following method:

A. A compound of the general formula $$R^O\text{-dibenzothiophene-}OH \quad \text{III}$$

wherein $R^o$ is as defined above, $R^o$ and the hydroxyl group being in the same or different benzene rings, is reacted with a compound of the general formula $$\text{HO}-\underset{R^2}{\overset{R^1}{C}}-\underset{\text{Hal}}{\overset{\text{Hal}}{C}}-\text{Hal} \quad \text{IV}$$

wherein $R^1$ and $R^2$ are as defined above and Hal is a chlorine, bromine or iodine atom; in the presence of a base, to produce a compound of formula I in which $R^3$ represents a hydrogen atom, and, if desired, converting this compound by methods known per se, to an alkyl ester. In the formula IV above Hal is preferably a chlorine atom. The base is preferably an alkali metal hydroxide, hydride or alkoxide, e.g. KOH, NaOH, NaH or $NaOC_2H_5$, preferably KOH, and the reaction is preferably conducted in organic solvents such as ethanol, acetone or the like.

The acid of the formula I above having $R^3$=hydrogen can, if desired, by methods known per se be converted to a pharmaceutically acceptable salt thereof by reaction with an appropriate base. The compounds of the formula I above can also, in cases when $R^1$ and $R^2$ are different, if desired, by methods known per se, be converted to an optically pure isomer thereof.

The following compounds can be mentioned as examples of compounds included in the present invention:

2-(2-dibenzothiophenoxy)-2-methylpropionic acid,
2-(3-dibenzothiophenoxy)-2-methylpropionic acid,
2-(4-dibenzothiophenoxy)-2-methylpropionoc acid,
2-(1-chloro-4-dibenzothiophenoxy)-2-methylpropionic acid,
2-(3-chloro-4-dibenzothiophenoxy)-2-methylpropionic acid,
2-(6-chloro-4-dibenzothiophenoxy)-2-methylpropionic acid,
2-(6-methoxy-4-dibenzothiophenoxy)-2-methylpropionic acid,
2-(3-methoxy-4-dibenzothiophenoxy)-2-methylpropionic acid and
2-(6-chloro-3-dibenzothiophenoxy)-2-methylpropionic acid, as well as their corresponding lower alkyl esters, e.g. the esters formed with ethanol, and their corresponding pharmaceutically acceptable salts.

In clinical practice the compounds of the present invention will normally be administered orally or by injection in the form of a pharmaceutical preparation comprising the active ingredient in the form of the original compound or optionally in the form of a pharmaceutically acceptable salt thereof, in association with a pharmaceutically acceptable carrier which may be a solid, semisolid or liquid diluent or an ingestible capsule, and such preparations comprise a further aspect of the invention. Usually the active substance will comprise between 0.1 and 95% by weight of the preparation, for example between 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes and compressed to form tablets or centers for dragees. If dragees are required, the centers may be coated, for example with concentrated sugar solutions which may contain gum arabic, talc and/or titanium dioxide, or alternatively with a lacquer dissolved in easily volatile organic solvents or mixtures or organic solvents. Dyestuffs can be added to these coatings, for example, to distinguish between different contents of active substance. For the preparation of soft gelatine capsules (pearl-shaped closed capsules) consisting of gelatine and, for example, glycerol, or similar closed capsules, the active substance may be admixed with a Carbowax. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid.

Liquid preparations for oral application may be in the form of syrups or suspensions, for example solutions containing from about 0.1% to 20% by weight of active substance sugar and a mixture of ethanol, water, glycerol, propylene glycol and optionally, aroma, saccharine and/or carboxymethylcellulose as a dispersing agent.

For parenteral application by injection preparations may comprise an aqueous solution of a water soluble pharmaceutically acceptable salt of the active acids according to the invention, desirably in a concentration of 0.5–10%, and optionally also a stabilizing agent and/or buffer substance in aqueous solution. Dosage units of the solution may advantageously be enclosed in ampoules.

The dosage used is dependent on individual requirements but the administration of about 1 g of the active substance three times a day may be recommended as therapeutical treatment of hyperlipaemia.

The invention is further illustrated by the following examples. Examples 1–3 relate to the preparation of starting materials to be used at the preparation of compounds according to the invention.

EXAMPLE 1

PREPARATION OF 4-HYDROXYDIBENZOTHIOPHENE

Dibenzothiophene (18.4 g, 0.10 mole) and N,N,N',N'-tetramethylethylenediamine (14.0 g, 0.12 mole) were dissolved in 200 ml dry ether. Butyl lithium (0.1 mole) in ether was added dropwise under stirring at room temperature. The reaction mixture was then refluxed for 1 hour. The mixture was cooled to −70°C and freshly distilled tributyl borate (23.0 g, 0.10 mole) was added. After stirring for 2 hours the solution was allowed to warm up to room temperature. Perhydrol (19 ml) was added dropwise and the mixture was refluxed for 1.5 hours. Hydrochloric acid was added and the ether was separated. The ether was washed with 10% ferrous ammonium sulphate solution and then extracted with sodium hydroxide solution. The alkaline aqueous solution was acidified and extracted with ether, which after evaporation gave 11.4 g (57%) beige crystals. Recrystallization from aqueous methanol gave light-brownish needles with m.p. 167°–168°.

EXAMPLE 2

PREPARATION OF 2-BROMODIBENZOTHIOPHENE

Dibenzothiophene (27.6 g, 0.15 mole) was dissolved in 125 ml chloroform. Bromine (24.0 g, 0.15 mole) in 25 ml chloroform was added dropwise and the mixture was kept at room temperature for 23 hours.

The chloroform was then washed with sodium thiosulphate solution, dried and evaporated to yield 37.7 g (96%) yellowish white crystals. Recrystallization from ethanol afforded white crystals with m.p. 117°–119°.

EXAMPLE 3

PREPARATION OF 2-HYDROXYDIBENZOTHIOPHENE

Butyl lithium (0.05 mole) in ether was added to 2-bromodibenzothiophene (13.15 g, 0.05 mole) in 150 ml dry ether at 0°C. The mixture was then cooled to −70° and freshly distilled tributyl borate (11.5 g, 0.05 mole) dissolved in 50 ml ether was added. The reaction mixture was stirred for 2 hours, and was then allowed to warm up to room temperature. Perhydrol (10 ml) was added and the mixture was refluxed for 1.5 hours. Hydrochloric acid was added and the organic phase was separated. The ether was washed with 10% ferrous ammonium sulphate solution and then extracted with sodium hydroxide solution. The alkaline aqueous solution was acidified and extracted with ether, which after evaporation gave 8.6 g (86%) of the desired product. Recrystallization from ligroin gave white crystals with m.p. 152°–155°.

EXAMPLE 4

PREPARATION OF 2-(4-DIBENZOTHIOPHENOXY)-2-METHYLPROPIONIC ACID

4-Hydroxydibenzothiophene (7.1 g, 0.0355 mole) and 1,1,1-trichloro-2-methyl-2-propanol (13.2 g, 0.071 mole) were dissolved in 80 ml acetone. The mixture was cooled to about 5°C and sodium hydroxide (11.4 g, 0.289 mole) was added in three portions over 1 hour. After addition of 80 ml acetone the mixture was refluxed for 4 hours. After evaporation of the solvent the residue was dissolved in water, acidified with hydrochloric acid and extracted with ether. Extraction of the etheral solution with sodium bicarbonate solution, acidification with hydrochloric acid and extraction of the aqueous phase with ether gave 9.5 g (93.5%) of the product. Recrystallization from benzene-ligroin (25:75) gave yellow crystals with m.p. 126°–128°.

Analysis: Found C 67.0, H 4.86, S 10.9. Calculated for $C_{16}H_{14}O_3S$: C 67.11, H 4.93, S 11.20.

2-(2-Dibenzothiophenoxy)-2-methylpropionic acid was prepared from 2-hydroxydibenzothiophene according to the above described procedure. The structure was confirmed by IR spectroscopy.

EXAMPLE 5

PREPARATION OF ETHYL 2-(4-DIBENZOTHIOPHENOXY)-2-METHYLPROPIONATE 2-(4-Dibenzothiophenoxy)-2-methylpropionic acid (9.5 g) was dissolved in 500 ml absolute ethanol. Dry hydrogen chloride was bubbled through for 3 hours, and the mixture was stored over night. After evaporation of the solvent, the residue was dissolved in 250 ml ether, washed with sodium bicarbonate solution, dried and evaporated to give 8.5 g of a brown liquid, b.p. 155–170/0.001 mm Hg.

Analysis: Found C 68.2, H 5.55, S 10.3. Calculated for $C_{18}H_{18}O_3S$: C 68.76, H 5.77, S 10.20.

Ethyl 2-(2-dibenzothiophenoxy)-2-methylpropionate was prepared in an analogous way in 54% yield. B.p. 158–166/0.005 mm Hg.

Analysis: Found C 68.3, H 5.53, S 9.94. Calculated for $C_{18}H_{18}O_3S$: C 68.76, H 5.77, S 10.20.

The following examples illustrates the preparation of some pharmaceutical compositions containing compounds according to the invention.

EXAMPLE 6

PREPARATION OF SOFT GELATINE CAPSULES 500 g of ethyl 2-(4-dibenzothiophenoxy-)-2-methylpropionate were mixed with 500 g of corn oil whereafter the mixture was filled in soft gelatine capsules, each capsules containing 100 mg of the mixture (i.e. 50 mg of active substance).

EXAMPLE 7

PREPARATION OF SOFT GELATINE CAPSULES 500 g of ethyl 2-(4-dibenzothiophenoxy)-2-methylpropionate were mixed with 750 g of peanut oil whereafter the mixture was filled in soft gelatine capsules, each capsule containing 125 mg of the mixture (i.e. 50 mg of active substance).

EXAMPLE 8

PREPARATION OF TABLETS 5 kg of ethyl 2-(4-dibenzothiophenoxy)-2-methylpropionate were mixed with 2 kg of silicon dioxide of the trade mark Aerosil, whereafter 4.5 kg of potato starch and 5 kg of lactose were mixed in and the mixture moistened with a starch paste prepared from 0.5 kg of potato starch and distilled water, whereafter the mixture was granulated through a sieve. The granulate was dried and sieved whereafter 0.2 kg of magnesium stearate were mixed in. Finally the mixture was pressed into tablets, each weighing 172 mg.

EXAMPLE 9

PREPARATION OF AN EMULSION 100 g of ethyl 2-(4-dibenzothiophenoxy)-2-methylpropionate were dissolved in 2500 g of peanut oil. From the solution thus obtained, 90 g of Gum Arabic, aroma and colour (q.s.) and 2500 g of water an emulsion was prepared.

EXAMPLE 10

PREPARATION OF A SYRUP 100 g of ethyl 2-(4-dibenzothiophenoxy)-2-methylpropionate were dissolved in 300 g of 95% ethanol where 300 g of glycerol, aroma and colour (q.s.) and water 1000 ml were mixed in. A syrup was thus obtained.

EXAMPLE 11

PREPARATION OF A SOLUTION 100 g of ethyl 2-(4-dibenzothiophenoxy)-2-methylpropionate were dissolved in 2000 g of polyoxyethylene sorbitan monooleate, whereafter aroma and colour (q.s.) and water to 5000 ml were mixed in. A drop solution was thus obtained.

EXAMPLE 12

PREPARATION OF EFFERVESCENT TABLETS 100 g of ethyl 2-(4-dibenzothiophenoxy)-2-methylpropionate, 140 g of finely divided citric acid, 110 g of finely divided sodium hydrogen carbonate, 3.5 g of magnesium stearate and aroma (q.s.) were mixed and the mixture was pressed into tablets, each containing 100 mg of active substance.

EXAMPLE 13

PREPARATION OF A DROP SOLUTION 100 g of ethyl 2-(4-dibenzothiophenoxy)-2-methyl-propionate were mixed with 300 g of ethanol, whereafter 300 g of glycerol, water to 1000 ml, aroma and colour (q.s.) and 0.1 N sodium hydroxide solution (to pH 4.5–5.5) were added while stirring. A drop solution was thus obtained.

EXAMPLE 14

PREPARATION OF A SUSTAINED RELEASE TABLET 200 g of ethyl 2-(4-dibenzothiophenoxy)-2-methyl-propionate were melted together with 50 g of stearic acid and 50 g of carnauba wax. The mixture thus obtained was cooled and ground to a particle size of at most 1 mm (diameter). The mass thus obtained was mixed with 5 g of magnesium stearate and pressed into tablets each weighing 305 mg. Each tablet thus contains 200 mg of active substance.

Biological tests

Effect on the level of cholesterol and triglycerides in rat plasma

Male rats of the Sprague-Dawley strain with a level of total cholesterol exceeding 180 mg per 100 ml plasma were used. Each group consisted of 6 rats. The rats were fed commercial rat chow for 6 days. The chow was obtained from Astra Ewos, Sodertalje, Sweden and was ground and supplemented with the test substance (0.3% w/w). Blood samples were taken immediately before the start of the experiment and after 6 days. The samples were taken by the morbital eye technique, i.e. out of the ophthalmic venous complex, without sacrificing the animals. The individual rats could thus serve as their own controls. Total cholesterol and triglycerides were determined by the method according to Technichon for Autoanalyzer, described in Technichon Laboratory Method File No. 24 and No. 78, respectively. The results are collected in Table 1 below, in which table compound No. 1 is 2-(4-dibenzothiophenoxy)-2-methyl-propionate. Atromidin is a compound of the formula

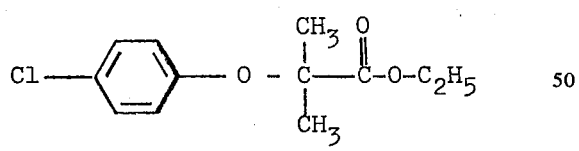

Table 1

| Compound No. | Plasma levels of total cholesterol and triglycerides after administration of test substance | |
|---|---|---|
| | Total cholesterol in % of initial values (day O) | Triglycerides in % of initial values (day O) |
| 1 | 57 ± 1 | 26 ± 2 |
| Atromidin | 81 ± 9 | 48 ± 2 |

Evaluation of the results from the biological tests

The purpose of the invention was to bring about substances which are capable of producing a combined lowering of both cholesterol and triglyceride concentrations in blood plasma of mammals. From the tests with rats (table 1) it is clear that the tested substance ethyl 2-(4-dibenzothiophenoxy)-2-methylpropionate, on comparison with Atromidin at the same dose, is capable of giving a more pronounced lowering of both cholesterol and triglyceride concentration. This is in itself advantageous and surprising but most important is that compounds according to the invention are capable of giving a clear decrease of both cholesterol and triglyceride levels and as can be seen from the tests, the clinically used substance Atromidin is capable of giving a decrease of triglyceride level but only a minor decrease of cholesterol level.

We claim:

1. A method for the treatment of excessive serum lipid concentrations in mammals comprising administering orally to a mammal in need thereof a therapeutically effective amount of a dibenzothiophene derivative having the formula

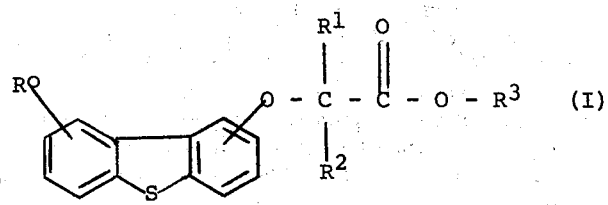

in which formula $R^0$ is selected from the group consisting of H, F, Cl, Br and $OCH_3$; $R^1$ and $R^2$ are the same or different and are selected from the group consisting of H and alkyl having 1–3 carbon atoms; $R^3$ is selected from the group consisting of H and alkyl having 1–3 carbon atoms; $R^0$ and the side chain containing the radicals $R^1$, $R^2$ and $R^3$ being on the same or different benzene ring.

2. The method according to claim 1 comprising administering orally a dibenzothiophene derivative having the formula

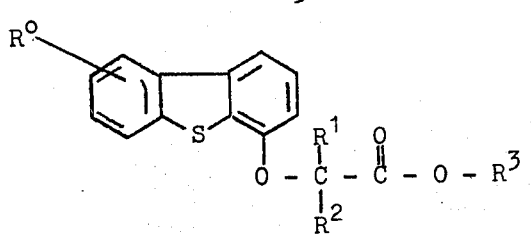

in which formula the groups $R^0$, $R^1$, $R^2$ and $R^3$ have the same meanings as defined in claim 1.

3. The method according to claim 1 comprising administering orally the dibenzothiophene derivative of formula I in which formula $R^0$ represents hydrogen; $R^1$ and $R^2$ are the same and represent methyl; and $R^3$ is selected from the group consisting of hydrogen and ethyl.

4. The method according to claim 1, comprising administering orally 2-(4-dibenzothiophenoxy)-2-methylpropionic acid.

5. The method according to claim 1 comprising administering orally ethyl 2-(4-dibenzothiophenoxy)-2-methylpropionate.

6. A composition for the treatment of excessive serum lipid concentrations in mammals comprising as an active ingredient a therapeutically effective amount of a dibenzothiophene derivative having the formula

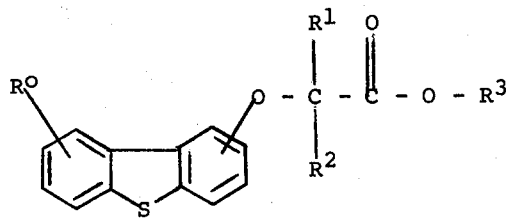

in which formula $R^0$ is selected from the group consisting of H, F, Cl, Br and $OCH_3$; $R^1$ and $R^2$ are the same or different and are selected from the group consisting of H and alkyl having 1–3 carbon atoms; $R^3$ is selected from the group consisting of H and alkyl having 1–3 carbon atoms; $R^0$ and the side chain containing the radicals $R^1$, $R^2$ and $R^3$, being on the same or different benzene ring; in combination with a pharmaceutical carrier.

7. The composition according to claim 6, comprising a therapeutically effective amount of a dibenzothiophene derivative having the formula

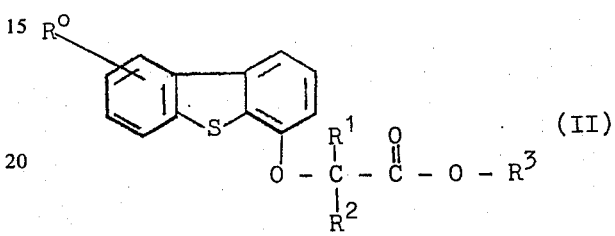

in which formula the groups $R^0$, $R^1$, $R^2$ and $R^3$ have the same meanings as defined in claim 6.

8. The composition according to claim 6, comprising a therapeutically effective amount of the dibenzothiophene derivative of formula I, in which formula $R^0$ represents hydrogen; $R^1$ and $R^2$ are the same and represent methyl; and $R^3$ is selected from the group consisting of hydrogen and ethyl.

9. The composition according to claim 6, comprising a therapeutically effective amount of 2-(4-dibenzothiophenoxy)-2-methylpropionic acid.

10. The composition according to claim 6 comprising a therapeutically effective amount of ethyl 2-(4-dibenzothiophenoxy)-2-methylpropionate.

* * * * *